(12) United States Patent
Borenstein et al.

(10) Patent No.: US 8,491,561 B2
(45) Date of Patent: *Jul. 23, 2013

(54) MICROMACHINED BILAYER UNIT OF ENGINEERED TISSUES

(75) Inventors: Jeffrey T. Borenstein, Holliston, MA (US); Eli Weinberg, Needham, MA (US); Brian K. Orrick, Cambridge, MA (US); Eleanor M. Pritchard, Cambridge, MA (US); Edward J. Barnard, Cambridge, MA (US); Nicholas J. Krebs, Boston, MA (US); Theodore Marentis, Boston, MA (US); Joseph P. Vacanti, Boston, MA (US); Mohammad Reza Kaazempur-Mofrad, Cambridge, MA (US)

(73) Assignees: The Charles Stark Draper Laboratory, Cambridge, MA (US); Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/857,489

(22) Filed: Aug. 16, 2010

(65) Prior Publication Data

US 2011/0056882 A1  Mar. 10, 2011

Related U.S. Application Data

(60) Division of application No. 10/983,213, filed on Nov. 5, 2004, now Pat. No. 7,776,021, which is a continuation-in-part of application No. 10/187,247, filed on Jun. 28, 2002, now Pat. No. 7,759,113.

(60) Provisional application No. 60/367,675, filed on Mar. 25, 2002.

(51) Int. Cl.
*C12M 3/06* (2006.01)

(52) U.S. Cl.
USPC ......... 604/406; 604/5.01; 604/6.09; 436/177; 436/178; 435/2; 435/283.1

(58) Field of Classification Search
None
See application file for complete search history.

(56) References Cited

U.S. PATENT DOCUMENTS

| 3,684,097 A | 8/1972 | Mathewson, Jr. et al. |
| 3,839,204 A | 10/1974 | Ingenito et al. |

(Continued)

FOREIGN PATENT DOCUMENTS

| EP | 0246675 A1 | 11/1987 |
| WO | WO 96/09423 | 3/1996 |

(Continued)

OTHER PUBLICATIONS

PCT/US03/29880, Sep. 23, 2003, The Massachusetts General Hospital/The Charles Stark Draper Laboratory/Massachusetts Institute of Technology.

(Continued)

*Primary Examiner* — Allison Ford
(74) *Attorney, Agent, or Firm* — Edwards Wildman Palmer LLP; Peter F. Corless; George N. Chaclas

(57) ABSTRACT

Methods and materials for making an apparatus which duplicates the functionality of a physiological system is provided.

13 Claims, 8 Drawing Sheets

U.S. PATENT DOCUMENTS

| | | | |
|---|---|---|---|
| 3,892,533 A | 7/1975 | Freedman et al. |
| 3,907,687 A | 9/1975 | Hoeltzenbein |
| 3,927,981 A | 12/1975 | Viannay et al. |
| 3,977,976 A | 8/1976 | Spaan et al. |
| 4,008,047 A | 2/1977 | Petersen |
| 4,176,069 A | 11/1979 | Metz et al. |
| 4,636,310 A | 1/1987 | Bellhouse |
| 4,666,668 A | 5/1987 | Lidorenko et al. |
| 5,034,188 A | 7/1991 | Nakanishi et al. |
| 5,061,620 A | 10/1991 | Tsukamoto et al. |
| 5,110,548 A | 5/1992 | Montevecchi et al. |
| 5,204,055 A | 4/1993 | Sachs et al. |
| 5,222,982 A | 6/1993 | Ommaya |
| 5,225,161 A | 7/1993 | Mathewson et al. |
| 5,263,924 A | 11/1993 | Mathewson |
| 5,266,480 A | 11/1993 | Naughton et al. |
| 5,316,724 A | 5/1994 | Mathewson et al. |
| 5,443,950 A | 8/1995 | Naughton et al. |
| 5,486,359 A | 1/1996 | Caplan et al. |
| 5,518,680 A | 5/1996 | Cima et al. |
| 5,626,759 A | 5/1997 | Krantz et al. |
| 5,665,596 A | 9/1997 | Mussi |
| 5,686,289 A | 11/1997 | Humes et al. |
| 5,695,717 A | 12/1997 | Polaschegg et al. |
| 5,785,964 A | 7/1998 | Naughton et al. |
| 5,843,780 A | 12/1998 | Thomson |
| 5,849,553 A | 12/1998 | Anderson et al. |
| 5,885,829 A | 3/1999 | Mooney et al. |
| 5,888,248 A | 3/1999 | Berg et al. |
| 5,906,828 A | 5/1999 | Cima et al. |
| 6,045,818 A | 4/2000 | Cima et al. |
| 6,107,043 A | 8/2000 | Jauregui et al. |
| 6,136,212 A | 10/2000 | Mastrangelo et al. |
| 6,139,574 A | 10/2000 | Vacanti et al. |
| 6,143,293 A | 11/2000 | Weiss et al. |
| 6,165,486 A | 12/2000 | Marra et al. |
| 6,183,781 B1 | 2/2001 | Burke |
| 6,197,575 B1 | 3/2001 | Griffith et al. |
| 6,200,802 B1 | 3/2001 | Greene et al. |
| 6,228,607 B1 | 5/2001 | Kersten et al. |
| 6,245,566 B1 | 6/2001 | Gearhart et al. |
| 6,287,558 B1 | 9/2001 | Lanza et al. |
| 6,372,482 B1 | 4/2002 | Mitrani et al. |
| 6,376,169 B1 | 4/2002 | Adams et al. |
| 6,455,311 B1 | 9/2002 | Vacanti |
| 6,458,275 B1 | 10/2002 | Shukla et al. |
| 6,479,064 B1 | 11/2002 | Atala |
| 6,479,072 B1 | 11/2002 | Morgan et al. |
| 6,525,242 B1 | 2/2003 | Wu et al. |
| 6,542,858 B1 | 4/2003 | Grass et al. |
| 6,547,994 B1 | 4/2003 | Monkhouse et al. |
| 6,573,063 B2 | 6/2003 | Hochman |
| 6,607,910 B1 | 8/2003 | Dimitrijevich et al. |
| 6,645,715 B1 | 11/2003 | Griffith et al. |
| 6,647,358 B2 | 11/2003 | Grass et al. |
| 6,942,873 B2 | 9/2005 | Russell et al. |
| 7,371,400 B2 | 5/2008 | Borenstein |
| 7,955,504 B1 | 6/2011 | Jovanovic et al. |
| 8,128,822 B2 | 3/2012 | Browning et al. |
| 8,137,554 B2 | 3/2012 | Jovanovic et al. |
| 2001/0041964 A1 | 11/2001 | Grass et al. |
| 2002/0010550 A1 | 1/2002 | Grass et al. |
| 2002/0013662 A1 | 1/2002 | Grass et al. |
| 2002/0035459 A1 | 3/2002 | Grass et al. |
| 2002/0055092 A1 | 5/2002 | Hochman |
| 2002/0061540 A1 | 5/2002 | Grass et al. |
| 2002/0090725 A1 | 7/2002 | Simpson et al. |
| 2002/0160471 A1 | 10/2002 | Kisiday et al. |
| 2002/0182241 A1 | 12/2002 | Borenstein et al. |
| 2003/0113708 A1 | 6/2003 | Flint et al. |
| 2003/0121594 A1 | 7/2003 | Brill |
| 2003/0124099 A1 | 7/2003 | Atala |
| 2003/0125252 A1 | 7/2003 | Underhill et al. |
| 2003/0129736 A1 | 7/2003 | Mitrani |
| 2003/0173965 A1 | 9/2003 | Oesingmann |
| 2003/0215941 A1 | 11/2003 | Campbell et al. |
| 2004/0057869 A1 | 3/2004 | Dingley |
| 2004/0084370 A1 | 5/2004 | Singh et al. |
| 2004/0147016 A1 | 7/2004 | Rowley et al. |
| 2005/0169962 A1 | 8/2005 | Bhatia et al. |
| 2005/0202557 A1 | 9/2005 | Vacanti et al. |
| 2007/0125489 A1 | 6/2007 | Paul et al. |
| 2010/0326914 A1 | 12/2010 | Drost et al. |
| 2010/0326916 A1 | 12/2010 | Wrazel et al. |
| 2012/0074062 A1 | 3/2012 | Jovanovic et al. |

FOREIGN PATENT DOCUMENTS

| | | |
|---|---|---|
| WO | WO-96/40002 | 12/1996 |
| WO | WO-0038758 | 7/2000 |
| WO | WO-0066036 | 11/2000 |
| WO | WO-01/11011 | 2/2001 |
| WO | WO-0238735 | 5/2002 |
| WO | WO-02076529 | 10/2002 |
| WO | WO 2003/061585 A3 | 7/2003 |
| WO | 2004020341 A2 | 3/2004 |

OTHER PUBLICATIONS

Supplementary European Search Report PCT/US04/01098, Mar. 13, 2007, The General Hosp. Corp.

International Search Report in PCT/US04/01098, Sep. 8, 2004, The General Hosp. Corp.

Written Opinion in PCT/US04/01098, Sep. 8, 2004, The General Hosp. Corp.

International Search Report in PCT/US00/11407, Dec. 6, 2000, Massachusetts General Hosp.

Written Opinion in PCT/US00/11407, Apr. 9, 2001, Massachusetts Gen. Hosp.

Supplementary European Search Report Application No. EP03718019, Jun. 2007, The General Hosp. Corp.

Jaeger, Introduction to Microelectronic Fabrication, Addison-Wesley Pub. Co., Reading, MA 1988.

Den Braber, et al, "Orientation of ECM protein deposition, fibroblast cytoskeleton, and attachment complex components on silicone microgrooved surfaces", Journal of Biomedical Materials Research, vol. 40, No. 2, May 1998, pp. 291-300.

O. Schueller, et al., *"Fabrication and Characterization of Glassy Carbon MEMS,"* Chem. Mater., 1997, vol. 9, pp. 1399-1406.

N. Patel, et al., *Spatially contolled cell engineering on biodegradable polymer surfaces*, The FASB Journal, vol. 12, Nov. 1998, pp. 1448-1454.

S. Huang, et al., "Control of Cyclin D1, p27Kip1, and Cell Cycle Progression in Human Capillary Endothelial Cells by Cell Shape and Cytoskeletal Tension," Molecular Biology of the Cell, Nov. 1998, vol. 9, pp. 3179-3193.

E. Delamarche, et al., "Patterned Delivery of Immunoglubulins to Surfaces Using Microfluidic Networks," Science, vol. 276, May 2, 1997, pp. 779-781.

C. Chen, et al., *"Geometric Control of Cell Life and Death,"* Science, May 30, 1997, vol. 276, pp. 1425-1428.

Y. Xia, et al., "Micromolding of Polymers in Capillaries: Applications in Microfabrication," Chem. Mater., 1996, vol. 8, pp. 1558-1567.

E. Delamarche, et al., "Microfluidic Networks for Chemical Patterning of Substrates: Design and Application to Bioassays," J. Am. Chem. Soc., 1998, vol. 120, pp. 500-508.

A. Folch, et al., "Molding of Deep Polydimethylsiloxane Microstructures for Microfluidics and Biological Applications," Journal of Biomechanical Engineering, Feb. 1999, vol. 121, pp. 28-34.

K. Heselmeyer, et al., "Gain of Chromosome 3q defines the transition from severe dysplasia to invasive carcinoma of the uterine cervix," Proc. Natl. Acad. Sci. USA, vol. 93, Jan. 1996, pp. 479-484.

E. Kim, et al., *"Polymer microstructures formed by moulding in capillaries,"* Nature, vol. 376, Aug. 17, 1995, pp. 581-584.

O. Schueller, et al., "Fabricaton of Glassy Carbon Microstructures by Pyrolisis of Microfabricated Polymeric Precursors," Adv. Mater., 1997, vol. 9, No. 6, pp. 477-480.

M. Trau, et al., "Microscopic patterning of orientated mesoscopic silica through guided growth," Nature, vol. 390, Dec. 1997, pp. 674-676.

M. Bailly, et al., "Regulation of Protrusion Shape and Adhesion to the Substratum during Chemotactic Responses of Mammalian Carcinoma Cells," Experimental Cell Research, vol. 241, (1998), pp. 285-299 (Article No. EX984031).

Thompson, et al; "A Novel Pulsatile, Laminar Flow Bioreactor for the Development of Tissue-Engineered Vascular Structures"; Tissue Engineering, vol. 8, No. 6, 2002, pp. 1083-1088.
Liu, et al; Characterization and Evaluation of Detoxification Functions or a Nontumorigenic Immortalized Porcine Hepatocyte Cell Line (HepLiu[1]); Cell Transplantation, vol. 8, 1999, pp. 219-232.
Griffith, et al; "In Vitro Organogenesis of Liver Tissue"; Bioartificial Organs, vol. 831 of the Annals of the New York Academy of Sciences, Dec. 31, 1997, pp. 382-397.
Ames, et al; "Methods for Detecting Carcinogens and Mutagens with the Salmonella/Mammalian-Micorsome Mutagenicity Test"; Mutation Research, 31 (1975), pp. 347-364.
Griffith, et al., Annals of Biomed. Eng., 26 (1998).
King, Kevin R.., et al., "Biodegradable Microfluidics", Advanced Materials, 2004, 16, No. 22, Nov. 18.
Shin, Michael et al., "Hybrid Bio/Artifical Microdevices", Biomedical Microdevices 6:4, 269-278, 2004.
Borenstein, Jeffrey T. et al., "Microfabrication Technology for Vascularized Tissue Engineering", Biomedical Microdevices 4:3, 167-175, 2002.
Fidkowski, Christina et al., "Endothelialized Microvasculature Based on a Biodegradable Elastomer", Tissue Engineering, vol. 11, No. 1/2, 2005.
Wang, Gou-Jen, et al., "Structure optimization of microvascular scaffolds", Biomed Microdevices (2005) 10: 51-58.
Kassab, Ghassan S. et al., "Morphometry of pig coronary arterial trees", American Physiological Society, 1993, 0363-6135/93.
Carraro, Amedeo et al., "In vitro analysis of a hepatic device with intrinsic microvascular-based channels", Biomed Microdevices (2008) 10:795-805.
Allen et al., Tissue Engineering (2002), vol. 8, No. 5, pp. 725-737.
Godbey et al., Ann NY Acad Sci (2002), vol. 961, pp. 10-26.
"Tissue" Merriam-Webster Online Dictionary, (2009), Merriam-Webster Online, May 21, 1009 URL; <http://www.m-w.com/dictionary/tissue>.
Marler J., et al., "Transplantation of cells in matrices for tissue regeneration", Advanced Drug Delivery Reviews, vol. 33, pp. 165-182, 1998.
Bell et al., Science 221, 1052 (1981).
Burke et al., Ann Surg 194, 413 (1981).
Langer, et al., Science 260, 920(1993).
Vacanti et al., Materials Research Society 252, 367 (1992).
Vacanti, et al., Lancet 354, 32 (1999).
Xu et al., Nat. Biotechnol., 19, 971 (2001).
Keller, et al., (1999) Exp. Hematol. 27:777-787.
Marti, et al., (1995) Nature. 375:322-325.
Prelle, et al., (2000) Biochem. Biophy. Res. Commun. 277:631-638.
Hardt, et al., (1985) Eur. J. Immunol. 15:472-478.
Huelsken, et al., (2001) Cell. 105:533-545.
Ji, et al., (2000) J. Bone Miner. Metab. 18:132-139.
Migliorati, et al., (1987) J. Immunol. 138:3618-3625.
Eghbali, et al., (1991) Proc. Natl. Acad. Sci. USA. 88:795-799.
Niijima, et al., (1995) J. Neurosci. 15:1180-1194.
Guo, et al., (1997) Dev. Biol. 184:61-69.
Ling, et al., (1998) Exp. Neurol. 149:411-423.
Lopez-Fernandez, et al., (2000) J. Biol. Chem. 275:21653-60.
Wang, et al., (1998) Leuk. Res. 13:1091-1097.
Lako, et al., (2001) Mech. Dev. 103:49-59.
Evans, et al., (1981) Nature 292: 154-156.
Matsui, et al., (1991) Nature 353:750-2.
Thomson, et al., (1995) Proc. Natl. Acad. Sci. USA 92:7844-8.
Thomson , et al., (1998) Science 282:1145-1147.
Shamblott, et al., (1998) Proc. Natl. Acad. Sci. USA 95:13726-31.
Mitaka, et al., Biochem Biophy Res Commun 214, 310 (1995).
Taneto, et al., Am Jpathol 148, 383 (1996).
Mitaka, et al., Hepatology 29, 111 (1999).
Teebken, et al., Eur J. Vasa Endovasc. Surg. 19, 381 (2000).
Ranucci, et al., Biomaterials 21, 783 (2000).
Burg, et al., J. Biomed. Mater. Res. 51, 642 (2000).
Rennie, J. Scientific American 280, 37 (1999).
Lysaght, et al., Tissue Eng 4(3), 231 (1998).
Amedee, et al., Differentiation, 58:157-164 (1994).
Burke, et al., Ann Surg 194, 413 (1981).
Compton, et al., Laboratory Investigation 60, 600 (1989).
Parenteau, et al., Journal of Cellular Biochemistry 45, 24 (1991).
Parenteau, et al., Biotechnology and Bioengineering 52, 3 (1996).
Purdue, et al., J. Burn Care Rehab 18, 52 (1997).

Hansbrough, et al., Clinical Plastic Surg 25, 402 (1998).
Vacanti, et al., Materials Research Society 252, 367 (1992).
Kane, et al., Biomaterials, 20, 2363 (1999).
Griffith, et al., Annals of Biomed. Eng. 831 (1997).
Folch, et al., Biotechnology Progress, 14, 388 (1998).
Eiselt, et al., Biotechnology. Prog. 14, 134 (1998).
Wang, et al., Nature Biotech 20, 602 (2002).
Runyan, et al., Semiconductor Integrated Circuit Processing Technology (Addison-Wesley Publishing Co., Reading, MA 01990); Proceedings of the IEEE Micro Electro Mechanical Systems Conference, 1987-1998.
Jansen, et al., The Black Silicon Method IV: The Fabrication of the Three-Dimensional Structures in Silicon with High Aspect Ratios for Scanning Probe Microscopy and Other Applications, IEEE Proceedings of Micro Electro Mechanical Systems Conference, pp. 88-93 (1995).
Frazier, et al., "Two dimensional metallic microelectrode arrays for extracellular stimulation and recording of neurons":, IEEE Proceedings of the Micro Electro Mechanical Systems Conference, pp. 195-200 (1993).
Lehmann, Porous Silicon—A New Material for MEMS:, IEEE Proceedings of the Micro Electro Mechnaical Systems Conference, pp. 1-6 (1996).
Laermer, et al., "Bosch Deep Silicon Etching: Improving Uniformity and Etch Rate for Advanced MEMS Applications", Micro Electro Mechnaical Systems, Orlando, FL, USA (Jan. 17-21, 1999).
Despont, et al., "High-Aspect-Ratio, Ultrathick, Negative-Tone Near-UV Photoresist for MEMS", Proc. of IEEE 10th Annual International Workshop on MEMS, Nagoya, Japan, pp. 518-522 (Jan. 26-30, 1997).
Henry, et al., "Micromachined Needles for the Transdermal Delivery of Drugs", Micro Electro Mechnanical Systems, Heidelberg, Germany, pp. 494-498 (Jan. 26-29, 1998).
A.A. Ayon, et al., "Tailoring Etch Directionality in a Deep Reactive Ion Etching Tool", J. Vac. Sci. Tech., B 18, 1412 (2000).
Sachs, et al., Manufacturing Review 5, 117-126 (1992).
Jo et al., SPIE 3877, 222 (1999).
Camporese, et al., IEEE Electron, Device Lett. EDL 2, 61 (1981).
Block, et al., J Cell Biol, 132, 1133 (1996).
Landry, et al., J Cell Biol, 101, 914 (1985).
Nishikawa, et al., Exp Cell Res. 223, 357 (1996).
Uyama, et al., Transplantation 55, 932 (1993).
Braber, Den, et al., J. Biomed. Matter. Res. 40, 291 (1998).
Aiken, et al., J. Pediatr Surg 25, 140 (1990).
Seglen, Methods Cell Biol 13, 29 (1976).
Schwerer, et al., Clinica Chemica Acta 163, 237 (1987).
Peterson, JE J Patol Bacteriol 89, 153 (1965).
Duffy, et al., Anal. Chem. 70, 4974 (1998).
Mitaka, et al., Gasroenterol Hepatol 13 Suppl., S70 (1998).
Tateno, et al., Am J Pathol 149, 1593 (1996).
Laconi, et al., Am J. Pathol 153, 319 (1998).
Hansborough et al., (1998) "Skin Replacements", Clin. Plast. Surg. 25(3): 407-23.
Henry, et al. (1998) "Micromachined Needles for the Transdermal Delivery of Drugs", The Eleventh Annual International Workshop on Micro Electro Mechanical Systems, Heidelberg, Germany, Jan. 25-29, 1998.
Kourepenis et al., (1998), "Performance of MEMS Inertial Sensors", Position Location and Navigation Symposium, Aerospace & Electronic Systems Society, Palm Springs, California, Apr. 20-23, 1996.
McWhorter, et al. (1997) "vol. 2: Micromachining and Trends for the Twenty-First Century" Handbook of Microlithography, Micromachinery and Microfabriation. Ed. P. Rai-Choudhury, Bellingham, WA: SPIE Press.
Renie, J. ed. (1999) Special Report: The promise of Tissue Engineering. Scientific American 280: 37.
Vacanti, et al. (1992) "Tissue-Inducing Biomaterials", Material Research Society Symposium Proceedings 252: 367.
Langer et al., (1993) "Tissue Engineering", Science 260 (5110): 920-6.
Langer et al., (1999) "Tissue Engineering: The Obstacles to Building New Organs for, Cells and Synthetic Polymers are Daunting but Surmountable", Scientific American 280, 86-89.
Sun Back et al., "Alternatives to Liver Transplantation: From Hepatocyte Transplantation to Tissue Engineering Organs", Gastroenterology 118: 438-442(2000).
U.S. Appl. No. 10/187,247, Vacanti et al., filed Jun. 28, 2002.

MICROMACHINED BILAYER UNIT OF ENGINEERED TISSUES

CROSS REFERENCE TO RELATED APPLICATION(S)

This application is a division of U.S. application Ser. No. 10/983,213, filed Nov. 5, 2004, issued as U.S. Pat. No. 7,776,021, which is a continuation-in-part of U.S. application Ser. No. 10/187,247, filed Jun. 28, 2002, which claims priority to U.S. provisional patent application Ser. No. 60/367,675, filed Mar. 25, 2002. The disclosures of each of these applications are incorporated by reference herein in their entireties.

Reference is made to U.S. application Ser. No. 10/038,891, filed Jan. 2, 2002, which claims priority to U.S. patent application Ser. No. 60/259,283, filed Jan. 2, 2001. Reference is made to U.S. application Ser. No. 09/560,480, filed Apr. 28, 2000, which claims priority to U.S. patent application Ser. No. 60/131,930 filed Apr. 30, 1999, and U.S. patent application Ser. No. 60/165,329, filed Nov. 12, 1999. The disclosures of each of these applications are incorporated by reference herein in their entireties.

INCORPORATION BY REFERENCE

Each of the foregoing applications and patents and articles, and each document cited or referenced in each of the foregoing applications and patents and articles, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein can be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

STATEMENT REGARDING GOVERNMENT INTEREST

The United States government has certain rights in this invention by virtue of grant number DAMD-17-02-2-0006 from the Department of the Army.

BACKGROUND OF THE INVENTION

1. Field of the Invention

The present invention generally relates to the fields of organ transplantation and reconstructive surgery, and to the new field of tissue engineering. More specifically, the present invention defines a new method and materials for providing a compact microfluidic system capable of filtering impurities and waste products from the blood stream to treat patients suffering from damaged, malfunctioning or failing vital organs, such as the kidney and liver.

2. Description of the Related Art

There are two principal therapeutic avenues for patients suffering from diseased, malfunctioning or failing vital organs responsible for blood filtration. One of these avenues involves organ assistance devices, such as the use of hemodialysis circuits in the renal unit of hospitals, or bridge therapy for liver failure such as the ELAD (Liver Assist Device). In the case of kidney dialysis, patients typically undergo 3 4-hour hemodialysis treatments per week in the clinic, each involving a trip to the clinic and a process in which the patient is connected to a large piece of equipment which filters waste products such as urea and creatinine from the blood stream while maintaining electrolyte, glucose and protein balances.

These treatments, while effective at sustaining life for ESRD (End-Stage Renal Disease) patients, are highly invasive, and are limited in effectiveness due to the non-physiological concentration profile of waste and impurities in the bloodstream. Namely, the concentration of urea, for example, becomes elevated well beyond levels in healthy patients for the 2-3 days between treatments, and is then lowered very rapidly during dialysis. These drastic excursions in concentration lead to complications and distress in dialysis patients, and the psychological impact of dialysis is associated with a sharp increase in suicide rates among the patient population. Most significantly, the long-term prognosis for ESRD patients on dialysis is poor, with 5-year survival rates of less than 20%.

The cost of these treatments is staggering, totaling approximately $12 Billion per year for the roughly 300,000 ESRD patients, or $40,000 per year per patient. For patients with liver failure, liver assist devices provide only bridge therapy, perhaps a few weeks at best, until a replacement liver is available.

The second avenue of treatment for patients with failing organs such as liver and kidney is transplantation, in which a donor organ is implanted into the patient from a variety of sources. These sources include cadaveric organs, which are in extremely limited supply, and therefore the number of patients on the waiting list for a vital organ is approaching 100,000 in the United States. Organ rejection by the recipient's immune system represents a huge challenge for the field of transplant medicine, because it severely limits the potential donor pool. Even when the donor is a match, recipients are consigned to a lifetime of immunosuppressive drugs, which are extremely expensive and are associated with a host of severe side effects. Other sources for donor tissue and organs are living donor transplants, which in the case of the kidney involve one organ from a donor with two healthy kidneys, or split liver transplants in which part of the liver of a healthy patient is transplanted into the recipient. Often involving family members, these transplants are typically safe for the donor but have led to well-documented cases in which previously healthy donors suffered lethal complications following transplant surgery.

Avenues beyond these two involve experimental procedures not yet ready for wide clinical practice. These include the use of artificial mechanical organs, such as the artificial fully implantable heart, biohybrid organs involving combinations of mechanical/artificial materials and devices and living cells and tissues, and fully natural tissue engineered organs which replace function.

The principal disadvantages of the two general approaches described above relate to the insufficient replacement of physiological organ function without serious limitations or complications. In the case of renal assist devices, specifically, the invasive, complex and discontinuous nature of the treatments limit their therapeutic value, because they do not provide patients with benefits concomitant with a healthy pair of kidneys. These disadvantages can be understood as being associated with limitations in the technology which insufficiently reproduce organ function, and limitations associated with cost, complexity and accessibility. The former set of challenges can be addressed by advances in dialysis involving either acellular processes (superior filtration, hemocompatibility, etc.) or cell-based processes (improvements in the resorption circuit which returns desired blood components to the body following ultrafiltration). The latter set of challenges relates to the fact that dialysis treatments are costly and labor-intensive, require frequent visits to the clinic and large, complex machines, and are not continuous because of the need for centralized dialysis clinics often distant from their patients.

Compact organ assist devices with continuous filtration that is physiologic in nature would provide enormous patient benefit. Moreover, a wearable, continuous device will reduce costs and labor associated with treatment, and will eliminate most visits to the clinic except for maintenance and monitoring. Accordingly, there is a need for improved systems.

SUMMARY OF THE INVENTION

The present invention provides the design, materials, fabrication and assembly processes to construct and implement a vital organ assist or even replacement device that overcomes the problems discussed above as well as other obstacles known in the art.

In particular, the present invention provides the design, materials, fabrication and assembly processes to construct and implement a microfabricated system to replace the blood filtering function of a vital organ such as the liver or kidney.

In one embodiment, the present invention provides an apparatus which duplicates the functionality of a physiological system, which includes first and second layers, each defining upper and lower surfaces. In specific embodiments, each layer can comprise a mold. A semi-permeable membrane can be secured to the first and second molds such that the upper surface of the membrane is secured adjacent to the lower surface of the first mold and the lower surface of the membrane is secured adjacent to the upper surface of the second mold.

In another embodiment, the apparatus is organized into a three-dimensional structure comprised of multiple two-dimensional layers, arranged in a repeating fashion, and stacked vertically in a total stack of at least 8 layers (e.g., stacks of bi-layers, each bi-layer consisting of an upper and lower surface). The present invention can comprise between about 50 and 2000 layers, more preferably between about 100 and 1000 layers and most preferably about 500 layers.

In yet another embodiment, the first and/or second molds can optionally include flow control patterns, such as interconnected microchannels cut into the mold, or disposed on a surface thereof. As used herein, the term "flow control pattern" refers to any feature capable of affecting flow, e.g., limiting or directing fluid flow, ranging from two-dimensional surface patterns to three-dimensional features such as posts, walls, channels or other raised structures. The flow control pattern can enhance diffusion and convection, among other things. The patterns in the first mold can be identical or non-identical to the pattern in the second mold. The pattern in the upper surface of the molds can be identical or non-identical to the pattern in the lower surface.

The apparatus can further comprise nutrient supply and excretion removal lines in fluid communication with the apparatus, pumping means for circulating fluid through the apparatus.

In a specific embodiment, the present invention provides an apparatus which duplicates the functionality of a physiological system comprising a first mold, a semi-permeable membrane, a second mold and a pumping means, wherein the first mold is fastened to the second mold and the semi-permeable membrane is disposed between the first and second molds, and wherein the first and/or second molds have means defining flow control patterns, and a pumping means for circulating fluid through the device.

In another specific embodiment, the flow control patterns can form fluidic chambers, supported by posts or walls. The fluidic chambers can be modeled after blood vessels, and can be from about 5 µm (small blood vessel dimension) in width and height to about 100 to 900 µm in width and height.

In yet another specific embodiment, the flow control patterns can form microchannels. Microchannels of the invention can be various sizes, for example, ranging from about 5 µm to about 5 mm in width and height, and extend longitudinally or latitudinally through the mold. The patterning of the microchannels can be controlled to form a microvascular network. The microchannels can be connected beginning from one or more inlets, expanding into more channels, and then converging back into one or more outlets.

In yet another specific embodiment, the first mold can comprise a microvascular network layer and the second mold can comprise a parenchymal layer having parenchymal cells. "Parenchymal cells" include the functional elements of an organ, as distinguished from the framework or stroma. Parenchymal cells can include but are not limited to smooth or skeletal muscle cells, myocytes, fibroblasts, chondrocytes, adipocytes, fibromyoblasts, ectodermal cells, including ductile and skin cells, hepatocytes, kidney cells, liver cells, cardiac cells, pancreatic islet cells, cells present in the intestine, and other parenchymal cells, osteoblasts and other cells forming bone or cartilage, and hematopoietic cells.

In yet another specific embodiment, the present invention provides an apparatus for the filtration of small molecules, comprising a first mold, a semi-permeable membrane, a second mold and a pumping means, wherein the first mold comprises a microvascular network, the second mold comprises parenchymal cells and the pumping means circulates fluid through the apparatus such that small molecules are removed from the microvascular network and passed to the parenchymal cells.

In other embodiments, the apparatus is acellular. In one embodiment, where the apparatus is acellular, the supply lines can be connected to a rehydration system. The rehydration system can comprise proximal tubule reabsorptive units of the kidney. Renal filtration involves diffusion and convection processes which result in the removal of important physiologic electrolytes (e.g., calcium, potassium and sodium), and proteins (e.g., the "middle molecules"), in addition to quantities of waste products (e.g., urea and creatinine) and water. Therefore, blood exiting the filtration portion of the kidney contains sub-optimal concentrations of these critical biomolecules. In this embodiment, the microfabricated filtration unit described herein is serially connected to a cell-based reabsorption unit which performs the physiologic function of restoring the concentration of electrolytes and other important biomolecules to desired levels once the blood has passed through the filtration device of the present invention. An engineered reabsorptive unit connected with a system constructed in accordance with the present invention can utilize cell function (i.e., proximal tubule cells of the kidney) or other known means to restore biomolecule concentrations to physiologic levels.

The surfaces of the molds are biocompatible can include a coating on the microchannels that promotes cell adhesion to the apparatus. The surfaces are preferably hemocompatible, or treated to promote hemocompatibility by, for example, the application of a hemocompatible film thereto or endothelialization of the surfaces. Blood clot-preventing compounds such as heparin can also be used to further facilitate the uninhibited flow of blood and long-term operation of the device, among other things.

In one embodiment, the membrane is made of a hemocompatible material.

Furthermore, the molds or membrane can include at least one growth factor covalently linked thereto at least one of the molds. The membrane can be biodegradable and have pores of between about 0.01 and about 20 μm. The molds can include through-holes, and may be fastened to the membrane or each other by a spin-glue process or a plasma bonding process, among other things.

The present invention is also directed to a method of fastening a semi-permeable membrane having an upper and an lower surface to a polymeric mold. The steps of such a method in accordance with the present invention can include: exposing the membrane and a polymeric film to oxygen plasma to attach the membrane and film to each other; separating the polymeric film from the membrane; and exposing the membrane and the mold to oxygen plasma to attach the surface of the mold.

This method may also include the step of exposing the membrane and a second mold to oxygen plasma to attach the surface of the mold.

The present invention is also directed to a method of fastening a semi-permeable membrane having an upper and a lower surface to a polymeric mold that includes the steps of: exposing the surface of the polymeric mold to the liquid state of the polymer used to form the polymeric mold; spinning the polymeric mold with the polymer liquid thereon; bringing the membrane in contact with the surface of the polymeric mold; and allowing the polymeric liquid in contact with the mold and membrane to set.

In the aforementioned method, the step of allowing the polymeric liquid in contact with the mold and membrane to set can further include elevating the surrounding temperature.

The systems and methods of the invention can be implanted into a subject to supplement or replace the biological function of a tissue or organ. Alternatively, the systems and methods can remain ex vivo, serving as extracorporeal devices to supplement or replace biological function.

Examples of tissues and organs which can be fabricated using these methods include, but are not restricted to, organs currently transplanted such as heart, liver, pancreas, lung, kidney and intestine. Other tissues such as muscle, bone, breast, reproductive and neural tissue could also be engineered.

These and other embodiments are disclosed or are obvious from and encompassed by, the following detailed description taken in conjunction with the figures as described below.

BRIEF DESCRIPTION OF THE DRAWINGS

The following detailed description, given by way of example, but not intended to limit the invention to specific embodiments described, may be understood in conjunction with the accompanying Figures, incorporated herein by reference, in which.

Figure 1:
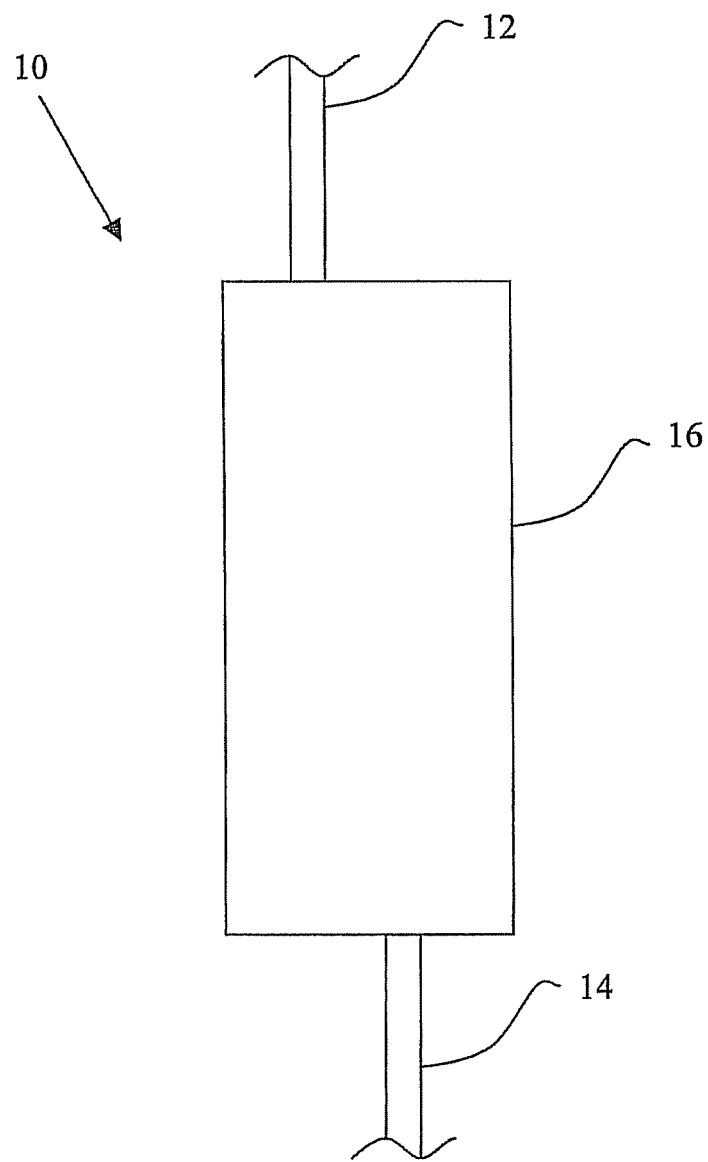
FIG. 1 is a schematic diagram of an exemplary organ assist or replacement device constructed in accordance with the present invention.

These and other features of the present invention will become more readily apparent to those having ordinary skill in the art from the following description of the preferred embodiments.

DETAILED DESCRIPTION OF THE INVENTION

In the following detailed description of the present invention, references are made to the accompanying drawings which form a part hereof, and in which is shown by way of simplified schematic illustrations specific embodiments in which the invention may be practiced. These drawings are not necessarily intended to accurately portray the entire system of the present invention, nor are they necessarily intended to be accurate portrayals of the size or shape of the elements of a system constructed in accordance with the present invention. However, one skilled in the art will readily appreciate that these figures along with the description herein are sufficient to enable those skilled in the art to practice the present invention.

Devices constructed in accordance with the present invention are designed to mimic proper anatomical and physiological conditions, and preferably provide even flow distribution, minimized flow resistance and a maximized surface area for transfer of oxygen nutrients and waste. Thus, devices constructed in accordance with this invention anticipate, and/or compensate therefore, non-Newtonian blood rheology and its multiphase nature, capillary occlusions causing local pressure drops, uneven velocity profiles and hematocrit distributions, among other things. Devices of the invention can optionally include flow control patterns to enhance diffusion and convection, among other things. Flow control patterns are known in the art, and described in U.S. Pat. Nos. 6,811,752, 6,810,713, 6,808,522, 6,808,075 and 6,802,342; as well as in Khademhosseini A, et al. (2004) Analytical Chemistry 76 (13): 3675-3681; Wang H Z, et al. (2003) J. Micromechanics and Microengineering 13 (6): 801-808; Kuksenok O, (2002) Physical Reviews E 65 (3): Art. No. 031502 Part 1; Delamarche E, et al. (1997) Science 276 (5313): 779-781; Stroock A D, Accounts of Chemical Research 36 (8): 597-604; Ng J M K, et al. (2002) Electrophoresis 23 (20): 3461-3473; and Stroock A D, (2002) Analytical Chemistry (20): 5306-5312, the contents each of which are incorporated herein by reference. Furthermore, the present invention utilizes microfabrication techniques to construct a system which, in addition to possessing the necessary features (e.g., capillary beds, nephrons, tissue, cultured cells, etc.) to duplicate the functionality of a specified physiological system, is also on a size scale similar to that physiological system.

The present disclosure provides the design, materials, fabrication and assembly processes to construct and implement a microfabricated system to replace the blood filtering function of a vital organ, such as the liver or kidney. The device can contain cells of the organ and a vascular network, with or without cells, or can be acellular. It should be understood that the present disclosure provides exemplary and preferred embodiments and uses of the present invention, and should not be limited thereto.

Extracorporeal and Implantable Devices

Devices constructed in accordance with the present invention can be implanted into a subject to supplement or replace the biological function of a tissue or organ. Alternatively, the invention can be adapted to comprise devices for uses in addition to the formation of implantable tissue. The devices can remain ex vivo, serving as extracorporeal devices to supplement or replace biological function. As used herein, the term "biological function" refers to the structural, mechanical or metabolic activity of a tissue or organ. Extracorporeal devices of the present invention can comprise hybrid devices suitable for both ex vivo and in vivo use. Any of the devices constructed in accordance with the present invention may provide partial support function, may extend the time between hospital treatments for patients on chronic organ support therapies, and can improve the quality of life between hospital treatments.

Commercially available extracorporeal devices do not incorporate the precise microfabrication capabilities offered by MEMS technology, and therefore function is limited by the resolution limits of current hollow fiber and membrane fabrication methods. Insertion of MEMS technology into this domain will provide major benefits for hemofiltering, dialysis and other applications. For example, the designs can be adapted to produce an extracorporeal renal dialysis device, an extracorporeal liver device, or an extracorporeal artificial lung device. Such devices may or may not be supported with living cells loaded or seeded into the device.

Referring now to the drawings wherein like reference numerals identify similar structural features of the invention, there is illustrated in FIG. 1, a microfluidic device constructed in accordance with a specific embodiment of the present invention and designated generally by the reference numeral 10.

Microfluidic device 10 includes an inlet 12 and an outlet 14 in fluid communication with a support body 16. Support body 16 substantially supports, and preferably encapsulates, a microfluidic network that enables device 10 to provide organ assist capabilities and is discussed in further detail herein below. Active devices that can provide flow and filtration control and optimization, such as pumps, valves, electric fields, transport devices, etc., can also be employed with microfluidic device 10.

Standard procedures may be employed to attach tubing connections for inlet 12 and outlet 14 to device 10 and external locations. Preferably, the process involves the bonding of tubing sections using either polymer glue materials, tight-fit connections, plasma bonding, or other means known in the art.

With particular regard to plasma bonding, support body 16 preferably includes a protective capsule. This can be an additional or optional step, which can provide further structural rigidity, as well as a more implantation-friendly shape for a device constructed in accordance with the present invention for such purpose, among other things. In such an embodiment, the material forming the capsule should be the same as the material from which the actual device is formed. This allows the two to unite into a single, continuous material when the capsule polymer has completely cured. The shape of the capsule is conferred by the mold from which it is created. Preferably, it is of a generally ovoid shape with connector tubes for inlet 12 and outlet 14 emerging from the tip of one of the long ends. The mold can be either rigid or conformal, and either single or multi-usage (i.e., the mold can be discarded after one molding process or it can be used multiple times to form several bodies of like shape).

Alternatively, balloons can be used as single-usage, conforming molds. The opening of a balloon is placed around the opening of a filtration flask, and the balloon is allowed to hang in the flask. Vacuum is drawn from a secondary inlet to the flask, causing the balloon to inflate. When the desired size is reached, the vacuum is maintained at its current pressure. Liquid polymer is poured to cover the remaining space and the top of the balloon is closed by means such as a string or similar closure. The polymer is allowed to cure and the balloon is then cut open to release the encased microfluidic network.

Another way to produce the capsule is to use a rigid, multi-usage mold with the desired shape. In one embodiment, the mold is constructed from two parts. A small hole is formed on the first or upper part of the mold to allow for polymer to be poured therein. One of the two longer sides should carry a small outlet hole for the connecting tubing. A thin layer of polymer is poured into the lower part of the mold and it is allowed to cure. The device is then positioned on a layer of polymer, and the connecting tubing is threaded through the appropriate hole of the upper part of the mold. The two parts are secured together by known means and the encasing is filled with liquid polymer through the hole at the top of the upper part of the mold.

In addition, the encasing mold can be a rigid, single-usage container such as a beaker or similar piece of glassware. The process is similar to the multi-usage mold described above. However, the mold can be sacrificed to release the device, which can prove to be an easier task to accomplish than preserving and reconditioning a multi-usage mold.

Materials and Methods

A two-dimensional (x, y) mold can be fabricated from a substrate material using high-resolution molding processes, such as micromachined wafer technology, thick photoresist processes, or other techniques, optionally micromachined, small dimensioned channels ("microchannels") can be patterned on the surface of the mold and connected for the circulation of fluid through a microfluidic network. Microchannels can comprise, for example, open-faced channels defined by walls extending from a tissue-defining surface of the substrate.

Materials suitable for forming the device and microfluidic network within support body 16 in accordance with the present invention preferably meet several criteria. First, such materials are preferably amenable to the microfabrication and assembly techniques such as those described herein below, including replica molding and bonding processes. These materials are preferably biocompatible, and not prone to fouling by such things as biofilms, proteins or other biological materials during use. Additionally, such materials preferably do not invoke an inflammatory or an immune system response.

Materials suitable for use as the substrate for the mold fabrication include, but are not limited to, poly-dimethylsiloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989). Combinations of these polymers may also be used.

In a preferred embodiment, polymers are selected based on the ability of the polymer to elicit the appropriate biological response from cells, for example, attachment, migration, proliferation and gene expression.

Solvents for most of the thermoplastic polymers disclosed herein are known, for example, methylene chloride or other organic solvents. Organic and aqueous solvents for protein and polysaccharide polymers are also known. The binder can be the same material as is used in conventional powder processing methods or can be designed to ultimately yield the same binder through chemical or physical changes that occur as a result of heating, photopolymerization, or catalysis.

Properties of the mold and/or polymer surface can be controlled and changed to impart desirable properties through the inclusion of materials on the mold or in polymer surface which alter cell attachment (e.g., by altering the surface charge or structure), porosity, flexibility or rigidity (which may be desirable to facilitate removal of tissue constructs). Moreover, advances in polymer chemistry can aid in the mechanical tasks of lifting and folding as well as the biologic tasks of adhesion and gene expression.

The preferred material for microfluidic devices of this embodiment is PDMS, which is a silicone rubber material which is moderately biocompatible and highly amenable to microfabrication and assembly. This material is not known for hemocompatibility, and therefore it is typically coated with materials such as collagen, Matrigel®, Vitrogen, or other substances which enhance biocompatibility.

In order to reduce clotting, the coated PDMS can be endothelialized to impart the microfluidic network with the same anti-thrombotic qualities as those provided to blood vessels by the presence of the endothelium. Further steps may be taken by pre-filtering of the blood at the front end of the device, either by removing blood components such as thrombocytes or by injecting compounds such as heparin to reduce clotting.

Alternative materials to PDMS for the structural component (e.g., channels for vascular and dialysate compartments of a renal dialysis device) can include polymethylmethacrylate (PMMA), polyethylene, or even biodegradable materials such as polyLactic (co-glycolic) acid (PLGA) or polyglycerol sebacate (PGS), among other things. Some of these materials, particularly PMMA and PGS, are known to be highly biocompatible, as well as hemocompatible. The biodegradable properties of PLGA and PGS, for instance, will limit the useful life of the device, but may be acceptable for systems in which the device is replaced on a regular basis (e.g., monthly) for maintenance purposes.

The filtration membrane material is preferably selected with care because of the significant and direct contact of blood with the membrane during the filtering process. Initial work in hemodialysis, for instance, employed the use of cellulose fibers, but these materials showed a propensity for clotting in dialysis systems. More recently, materials such as PMMA, polysulfone (PS) and polyethersulfone (PES) have been used for the hemodialysis membrane, with generally far superior results. Accordingly, the membrane can be made of a biologically compatible, nondegradable material such as cellulose, PolyDiMethylSiloxane (PDMS), PolyMethylMethacrylate (PMMA), PolyEtherSulfone (PES), PolySulfone (PS), PolyCarbonate (PC), or from a degradable material such as PLGA, PolyCaproLactone (PCL) or Biorubber, but the invention is not so limited.

Some exemplary devices constructed in accordance with the subject invention have used PDMS as the structural material of the microfluidic device while the membranes have been either polycarbonate (PC) or PES. The PC membrane has been used however it is not believed to have enhanced biocompatibility or hemocompatibility. For a presently preferred embodiment, the structural material is selected from endothelialized PDMS, PGS or PMMA, or a combination thereof, with the membrane being either PES or PMMA, or a combination thereof.

Some exemplary, non-limiting fabrication methods for manufacturing microfluidic networks for use with a device in accordance with the present invention are discussed below. In particular, polymer substrates having microfluidic networks thereon have been constructed using double-sided molding techniques. In conventional soft photolithography, a silicon wafer is first processed with traditional micromachining techniques to carry a certain pattern. The wafer is placed in a petri dish with the pattern facing upwards and the polymer in its liquid, non-crosslinked form is poured over the silicon mold. The polymer conforms to the shape of the mold and, with the help of heat or light, is converted to its solid, cross-linked state. The double-sided molding technique uses two silicon molds and sandwiches the polymer in between the two.

Materials other than silicon may also be used, however, one other consideration in this embodiment is that typical 500 μm thick silicon wafers may not provide sufficient mechanical strength for all applications and embodiments in accordance with the present invention. This is because, after the polymer has set, it becomes difficult to separate the wafer-polymerwafer sandwich without breaking the silicon molds. Therefore the use of thicker silicon wafers is preferred, such as, for example, 700 µm, 1 mm, 1.5 mm, or even thick glass wafers may be used to ensure safe separation of the molds from the cured polymer.

The two mold wafers may be fabricated using either conventional bulk silicon processing, such as described in the related, commonly assigned application, U.S. patent application Ser. No. 10/187,247. Alternatively, an epoxy resin process, which is also described in the aforementioned Application, can be used in which a thick photoresist directly serves as the mold and silicon micromachining is not involved. The aforementioned patent application is incorporated herein by reference.

The molds can carry the same or different patterns. Each mold is placed on a small pedestal, which sits in a large petri dish. The radius of the petri dish should be greater than the radius of the silicon mold to collect excess of polymer dripping from the sides of the mold. The pedestal can range from a small petri dish to a metallic stand. The key feature is that the radius of the pedestal should be sufficiently smaller than the radius of the silicon wafer, and the pedestal must be tall enough to allow for polymer poured in excess of the capacity of the mold surface to flow freely off the surface without trapping the mold in the petri dish after it has cured.

Spacers may be applied to one of the two molds. The spacers are thin, uniformly flat objects that will keep the two molds apart from each other and allow a polymer layer of uniform thickness to go between them. They control the thickness of the resulting polymer layer. A preferred embodiment utilizes four washers (e.g., Rockford 508 washers) with a measured thickness of 1.2 mm+/−0.015 mm. Alternatively, one may deploy small silicon wafer pieces, bringing the thickness of the mold layer down to 500 µm. It is preferably that the spacers does not prevent the polymer from flowing radially away from the mold as the two molds are brought together. It is also preferably that the spacer is placed on mold "dead-space", which bears no raised features. Washers may be used to ensure uniform separation between the two molds across the entire area of the silicon wafer.

In the next step, the polymer is poured over the mold. Roughly 15-20 mL of polymer is sufficient to completely cover the mold. After letting the molds settle for a sufficient period to ensure complete coverage, both are placed in a vacuum chamber. A vacuum is then drawn, and the molds degas for about one hour. This removes all the microbubbles from the polymer, which may have either originated from mixing the polymer with the curing agent, or were trapped in the features of the mold when pouring the polymer over them.

After some time has passed, (e.g., about one hour) the molds are taken out of the vacuum. The mold is then lifted without the spacers, and quickly flipped so that its features and the polymer face downwards. It can be positioned over the mold with the washers. The molds are then placed proximate to one another, in that the end of the upper mold is situated next the respective end of the lower mold so that the silicon surface makes contact with the washer. The upper mold is then slowly lowered so that the two polymer layers come in complete contact with each other. A gentle force is applied to push the excess polymer out and complete the sandwich.

The large petri dish carrying the pedestal, mold and polymer mold layer is placed in an oven at a temperature of about 65° C. for about 20 minutes. Because of the minute thickness of the polymer compared to the surface area of the silicon wafer this time is sufficient for complete curing. The petri dish is then taken out of the oven and allowed to cool.

The next step is to detach the two molds from the polymer mold layer. A very thin, blunt object, such as flat spatula, is used as a wedge in the plane between the silicon and the polymer across the whole circumference of the mold, on both molds. The spatula can be inserted just a few millimeters to sufficiently ensure release. It is critical to completely separate the washers from the molds on both sides because that is where the highest stress concentration takes place, and where the mold layer is most likely to tear upon release. Insertion of the spatula between the top mold and the washer along with a gentle, constant force for a few seconds, is the preferred method for accomplishing this task. This same process is then repeated on all spacers up until the top mold has lifted off from the polymer.

Figure 2:
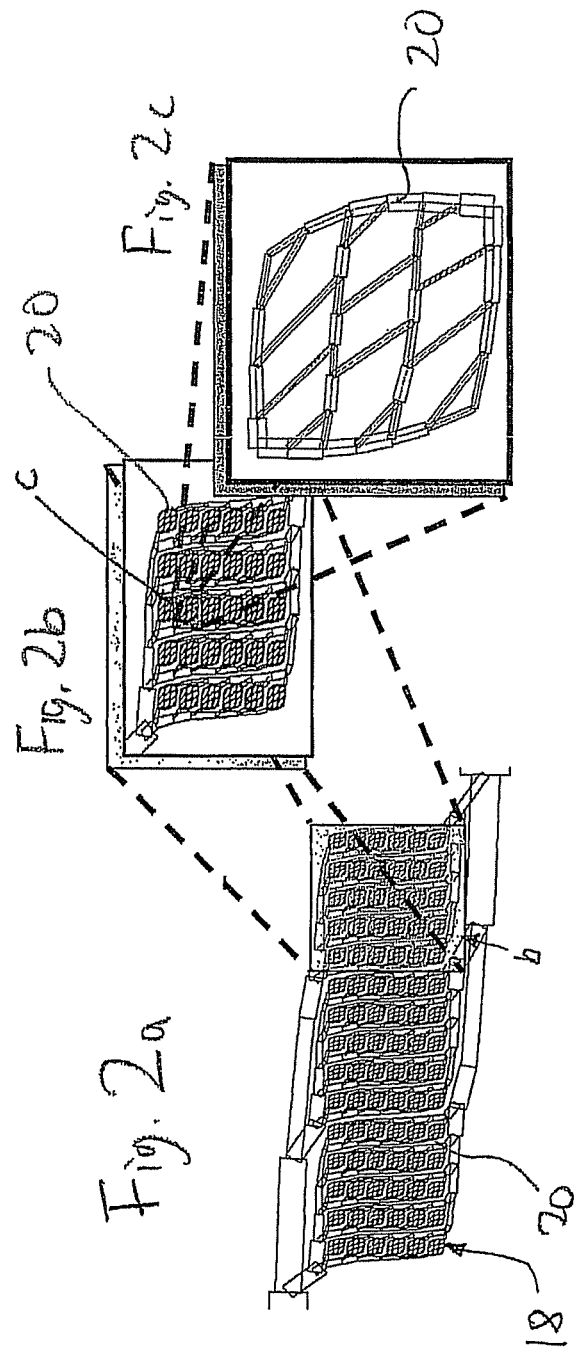
FIG. 2*a* is a schematic view of a microfluidic network formed on a polymer film according to an embodiment of the present invention.
FIG. 2*b* is a closeup view of the area of FIG. 2*a* designated by the letter "b," illustrating a portion of the microfluidic network of FIG. 2*a* in detail.
FIG. 2*c* is a closeup view of the area of FIG. 2*b* designated by the letter "c," illustrating a portion of the microfluidic network of FIG. 2*a* in detail.

The same process is then repeated for the lower mold. Note that the order of starting with the top mold and following with the lower one is important to ensure separation without breaking the molds or tearing the mold layer. An example of a polymer mold layer 18 having pluralities of microvascular networks 20 formed thereon by the microfabrication techniques of the present invention described herein is shown in FIGS. 2a-c.

Membrane

A filtration membrane can be used to separate the first mold from the second mold of the present invention. Preferably, the membrane is semi-permeable and the pore size of the membrane is smaller than the cell diameters, thus, cells will not be able to pass through (i.e., a low permeability for animal cells), while low molecular weight nutrients and fluids can pass through (i.e., a high permeability for nutrients), thereby providing adequate cell-to-cell signaling. Cell sizes vary but in general, they are in the range of microns. For example, a red blood cell has a diameter of 8 µm. Preferably, the average membrane pore size is on a submicron-scale to ensure effective screening of the cells.

Semi-permeable membranes of the present invention comprise a wide array of different membrane types and morphologies, which can be classified as follows:

(1) Track-etch membranes consisting of cylindrical through-holes in a dense polymer matrix. These membranes are typically made by ion-etching; or
(2) Fibrous membranes made by various deposition techniques of polymeric fibers. While these membranes do not have a well-defined pore topology, production methods have been sufficiently refined so that fibrous membranes have specific molecular weight cut-offs.

Track-etch type membranes are preferred, as they limit the fluid motion in one direction. Preferably, fluid motion is in the vertical direction. Fibrous membranes permit fluid motion both laterally and vertically.

Figure 3:
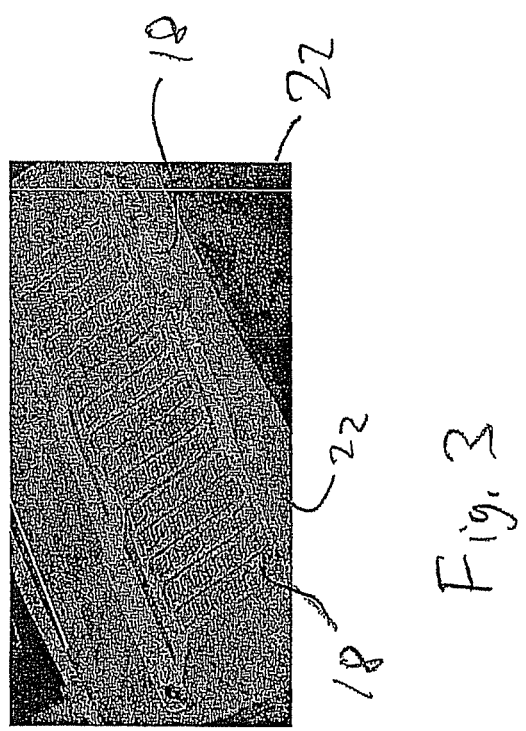
FIG. 3 is a schematic view of a bilayer system, incorporating a microfluidic network as shown in FIG. 2*a* and disposed on a porous membrane, in accordance with an embodiment of the present invention.

In the exemplary embodiment discussed herein, once mold layers 18 have been fabricated, they are attached to a porous filtration membrane 22, an example of which is shown in FIG. 3. Plasma bonding is one commonly employed procedure that accomplishes polymer-to-polymer bonding for films such as polydimethylsiloxane (PDMS). Plasma bonding is a well-known process for modifying the surface of PDMS to increase the density of hydroxyl groups and the hydrophilicity of the material, which tends towards a more hydrophobic behavior without plasma treatment. Typical plasma parameters include the use of pure oxygen gas, flowing in a vacuum oven at a pressure of about 200 mTorr, for periods of about 30-60 seconds and power levels of roughly 50-100 Watts. The plasma treatment is used to expose the surfaces of the layers to be bonded.

The first step is to expose the membrane and a blank piece of PDMS to oxygen plasma. Next, the membrane is attached to the blank piece of PDMS. Once the two surfaces have been attached together, the membrane is peeled from the blank PDMS. The membrane is then exposed to oxygen plasma again, along with a layer of PDMS with microchannels, and these two pieces are attached together. Finally, the membrane/microchannel sandwich and the opposing microchannel layer are exposed to oxygen plasma and then attached together, forming the mold layer with the semipermeable membrane.

The spin-glue process is a viable alternative to the plasma bonding technique and achieves polymer-to-membrane bonding. In this process, a polymer mold layer 18 (or single layer) is positioned with the side holding the design of interest upwards. A small portion (about 1-2 ml) of the liquid state of the same polymer the mold layer 18 is made of is poured onto the mold layer 18. This is counterintuitive since the architectural features of interest (e.g., microfluidic channels) are buried under the liquid polymer "glue".

The mold layer 18 is then positioned on a spinner chuck and spun for 1 minute at a set speed in the range of about 2000 rpm to about 3500 rpm. Spinning provides a conformal coating over the entire top surface of the mold layer 18, while exposing all the channels previously buried under the glue. The spin speed defines the thickness of the glue. A spin curve (i.e., what spin speed corresponds to what thickness) can be readily established.

Mold layer 18 is taken out of the spinner and put on a flat surface covered with laboratory wipes. Membrane 22 (or another layer) is slowly brought in proximity with mold layer 18. One can either make contact by hand, or gently release membrane 22 in very close proximity to mold layer 18. With pressure from the center of mold layer 18 to the periphery, membrane 22 is gently contacted to ensure it contacts everywhere with the polymer. Care should be taken not to apply too much force, which would cause membrane 22 to touch down at the bottom of the channels, pick up glue and potentially occlude.

The polymer glue needs to set, and thus, the device can be left at room temperature for approximately two hours or put in an oven at about 65° C. for about five minutes, among other things. However, in using the latter technique, buckling of the device may be observed. This is because the polymer expands more than membrane 22 when heated. This can be advantageous, as a method of quality control, that is, if buckling is observed then the polymer and membrane 22 have been successfully bonded to each other. Buckling helps relax the stress produced by the differential expansion of the two materials upon heating only if the two materials are tightly bonded to each other.

The same process may be used as many times as necessary to bond all mold layers 18 to membranes 22 and to each other, thus creating a multilayer device. Preferably, mold layer 18 on which glue has been spun on needs to remain with the glue facing upwards, and the layer/membrane without the glue is preferably facing downward.

Mathematical Modeling for Devices of the Present Invention

The first step in this modeling method is to create a hypothetical "mesh" depicting the device. Once the mesh is constructed, time-varying behavior is modeled in a series of discrete timesteps. At each timestep, three sets of calculations are made. First, the boundary conditions and concentration distribution are used to calculate solvent velocities throughout the device. Second, the solvent velocities are used to determine the solute fluxes. Third, the solute fluxes are used to update the concentration distribution. The next timestep is then started by calculating the solvent velocities from the boundary conditions and the modified concentration distribution.

An orthogonal mesh is created, filling the space of the device. The mesh consists of a set of nodes, each specifying an (x,y,z) location, and a set of vessels. Each vessel connects two nodes and is specified by those two nodes. The mesh spacing is uniform.

Inlets and outlets to the device are included by defining appropriate nodes as inlet and outlet nodes, and their associated vessels as inlet and outlet vessels. Inlets have specified solvent flow rates and outlets allow solvent and solutes to flow out of the device.

Each vessel is assigned a set of conductances $L_1$, $L_2$, $L_3$, and $L_4$ representing the mass transport properties of the device in the region of that vessel. These conductances will be discussed further in the following sections. An initial concentration distribution is specified by assigning an initial concentration value at each node.

Calculation of Solvent Fluxes

The solvent velocity between any two points can be calculated knowing the pressures and concentrations at those two points, and the conductances between the points. Solvent flow has two components, convection and osmosis. Convection contributes a flux $$\Phi_C = L_1(P_1 - P_2), \quad \text{(Eq. 1)}$$

where $L_1$ is the hydraulic permeability between the two points and $P_1$ and $P_2$ are the pressures at the first and second point, respectively. The hydraulic permeability can be calculated from geometry: if the points are separated by porous material, $L_1$ is representative of the Darcy flow through the material. If the points are separated by a duct, such as a circular vessel or rectangular vessel, $L_1$ represents the laminar flow solution of the duct. Any conductance between two points is given by the conductance of the vessel connecting those points.

The osmotic contribution to the flux is $$\Phi_{OS} = \sum_{j=1}^{N} \sigma_j L_1 RT(C_{j2} - C_{j1}), \quad \text{(Eq. 2)}$$

where $\sigma_1$ is the reflection coefficient of the material to the solute j, R is the universal gas constant, T is the absolute temperature, and $C_{j1}$ and $C_{j2}$ are the concentrations of solute j at the first and second point, respectively. We are summing the effects of N solutes.

The total volumetric flux of the solvent is the sum of the convective and osmotic components, $$\Phi_V = L_1(P_1 - P_2) + \sum_{j=1}^{N} \sigma_j L_1 RT(C_{j2} - C_{j1}). \quad \text{(Eq. 3)}$$

This equation cannot be used to directly calculate the fluxes since the pressures are unknown. The flux must be converted to flow rate q by multiplying by an area, $$q = A_c \Phi_V, \quad \text{(Eq. 4)}$$

where $A_c$ is an appropriate area, the mesh spacing squared. Flow is conserved through any intersection of vessels, so continuity can be applied to cancel the flow rates and create a matrix equation where the pressures are the only unknowns, $$[L_1 A_c][P] = [L_2 \Delta C A_c] + [BC], \quad \text{(Eq. 5)}$$

where $[L_1 A_c]$ is a nodal matrix describing the connectivity of the mesh, [P] is a vector of the unknown node pressures, $[L_2 \Delta CA_c]$ a vector describing the osmotic effects, and [BC] is a vector describing flowrate boundary conditions. Internal forced or pumped flows can also be included in [BC]. If there are K nodes, the matrix is (K×K) and the vectors are all (K×1). This is a parabolic system of equations and can be solved by LU factorization to compute the unknown pressures. Then Eq. 3 can be used for each vessel to determine the solvent flux at that vessel.

Solute flux is the sum of convective and diffusive terms. The convective flux of solvent j is $$\Phi_{Cj} = \overline{C}_j \Phi_V, \quad \text{(Eq. 6)}$$

where $\overline{C}_j$ is an average concentration between points 1 and 2 and the solvent flux has been calculated above.

The diffuse flux is given by Fick's Law, $$\Phi_{Dj} = D_j (C_{j1} - C_{j2}), \quad \text{(Eq. 7)}$$

where $D_j$ is the diffusion coefficient of solute j in the material between points 1 and 2.

Total volumetric solute flux is a sum of the convective and diffusive terms, $$\Phi_j = \overline{C}_j \Phi_V + D_j (C_1 - C_2) \quad \text{(Eq. 8)}$$

The solute fluxes can be calculated directly for each vessel once the concentrations and solvent fluxes are known.

Update of Concentrations

Concentration of solvent j at any node changes in time as described by $$\frac{dC_j}{dt} + U_j \frac{dC_j}{dx} = 0, \quad \text{(Eq. 9)}$$

where U is the solvent speed, equal to $\Phi_j/C_j$. This equation is discretized on the mesh so the concentration at a node, at any time t+Δt, can be calculated from the concentrations and fluxes in the nodes and vessels around it. With $U_j$ varying in space, this equation is a variable-coefficient linear hyperbolic equation known as the Color Equation. Care must be taken to use a method that does not introduce numerical diffusion to the solution. Here, a high-resolution Gudunov method with Superbee flux limiting is used. This method is extended to use in three dimensions by a subinterval method. This method is run for every node, updating the concentrations throughout the device at each timestep.

Iteration

Once the concentration has been updated, the simulation returns to the first step. The vector $[L_2 \Delta CA_c]$ is modified by using the updated concentrations, and all three stages are repeated. The three stages taken together represent one time step.

Initial Results

The above methods have been implemented in Matlab and run in test cases up to 200 nodes on a mesh representing a mold layer design with inlet and outlet on each layer. The method is convergent in various combinations of convection, osmosis, diffusion, and forced flows.

EXAMPLES AND SPECIFIC EMBODIMENTS

Results obtained on single bilayer devices tested for ultrafiltration of urea and creatinine are described in the following discussion. Single bilayer devices were constructed using some or all of the techniques described in the above fabrication section.

Figure 4:
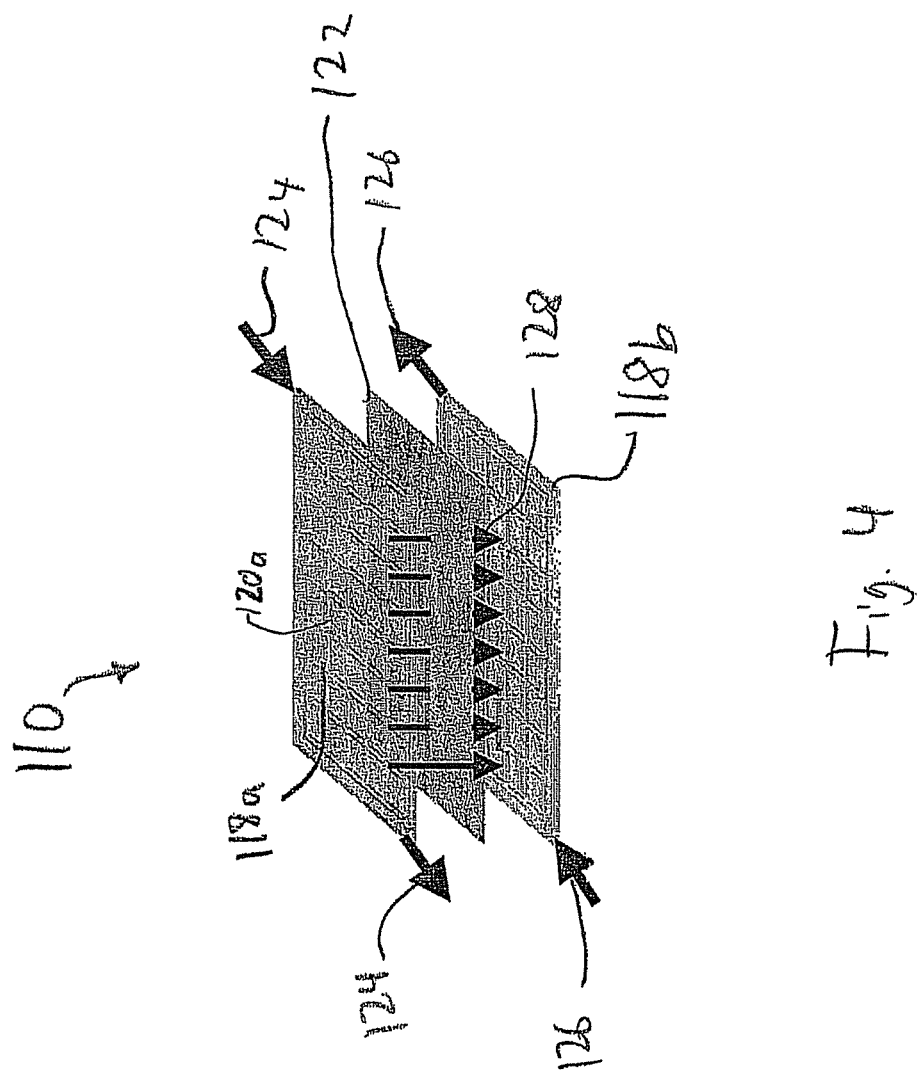
FIG. 4 is a schematic diagram of a single pass, countercurrent system constructed in accordance with an embodiment of the present invention which includes mold layers, including microfluidic networks embedded therein, separated by a microporous membrane and illustrates the flow of blood and dialysate streams through the system.

A device 110 of the present invention is shown schematically in FIG. 4. Device 110 includes a first mold layer 118a and a second layer 118b separated by a microporous membrane 122. In one embodiment, the first mold layer 118a can comprise a microvascular network, including microchannels that direct flow through chambers and conduits, and the second mold layer 118b can comprise a parenchymal layer having cells. The term "microvascular network," as used herein, refers to fluidic network modeled after a physiologic vasculature, such as a capillary network. The microvascular network either may or may not consist of an actual endothelium. In another embodiment, the mold layers are acellular (e.g., no cells are cultured within the layers).

In a specific embodiment, the microvascular network is comprised of small and/or midsized vessels and connecting the vessels within one layer to at least one additional layer with vertical links, as described by PCT/US03/29880, filed on Sep. 23, 2003, the contents of which are incorporated herein by reference. In this embodiment, channels carrying blood (e.g., a vascular network) would be arranged proximally to channels containing dialysate in the same layer, such that impurities in the bloodstream would be filtered laterally across an intervening membrane into the dialysate channel network, rather than vertically. Mass transport of the filtered blood products would occur through a set of "vertical pores" rather than through a horizontally positioned semipermeable membrane. The geometries of the vertical pores can be controlled to enable efficient hemofiltration.

In this system, countercurrent flows of blood and dialysate streams into and out of device 110 are illustrated by arrows 124 and 126, respectively. Ultrafiltration flow through microporous membrane 122 within device 110, from first mold layer 118a to second mold layer 118b, is illustrated by arrows 128.

To study the ultrafiltration capabilities of a device having a microvascular mold layer and a parenchymal layer, the clearances of urea and creatinine from the vascular/"blood" stream 124 into the parenchymal/"dialysate" stream 126 were examined at varying flow rates under single-pass countercurrent conditions. For the purposes of this exercise, the parenchymal layer as well as the microvascular mold layer was empty, i.e., acellular. Microvasculature 120a refers to a microfluidic network modeled after a vascular network in order to mimic the capillary networks developed for vascularized tissues as the flow patter for the blood, among other things. The vascular fluid in flow stream 124 consisted of ultra-pure water containing dissolved urea and creatinine at concentrations of 400 and 200 mg/dl respectively, while the parenchymal fluid of stream 126 consisted of only ultra-pure water. The urea and creatinine solutions were pumped through the vascular layer 118a containing the microvasculature 120a and the ultra-pure water/"dialysate" was pumped through the parenchymal layer 118b.

The flow-rate ratios of vascular flow ($Q_B$), parenchymal flow ($Q_D$) and individual flow rates used for each solute were approximately at a 2:1 ratio ($Q_B:Q_D$) at 0.9 and 2.0 ml/hr respectively, 1:1 ($Q_B:Q_D$) at 1.0 ml/hr, and 1:1 ($Q_B:Q_D$) at 2.0 ml/hr. In an incubator at 37° C., a syringe pump was used to administer each fluid into its respective layer, under conditions of countercurrent, single-pass flow.

Figure 5:
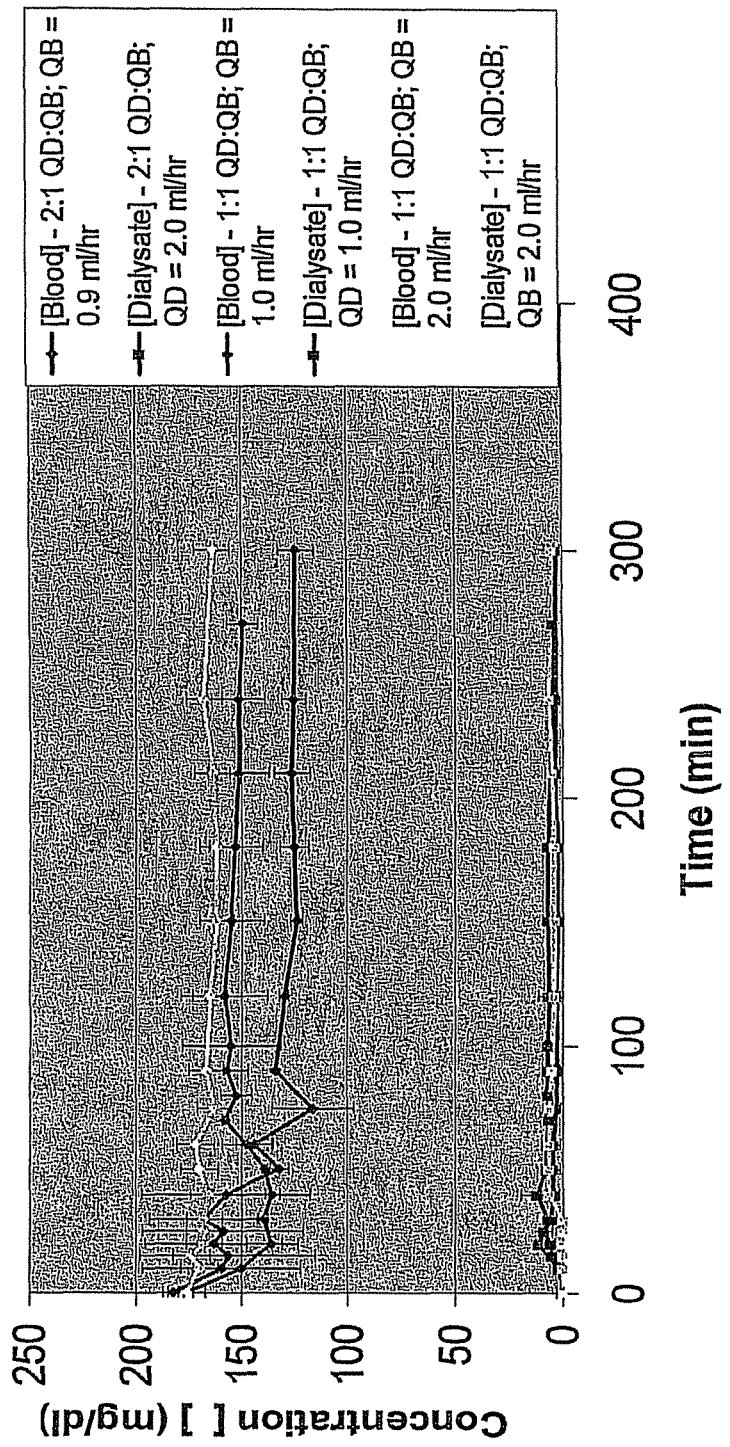
FIG. 5 is a graph depicting urea concentration vs. time at varying flowrate conditions using polycarbonate membranes in exemplary ultrafiltration experiments using the system of FIG. 4.
Figure 6:
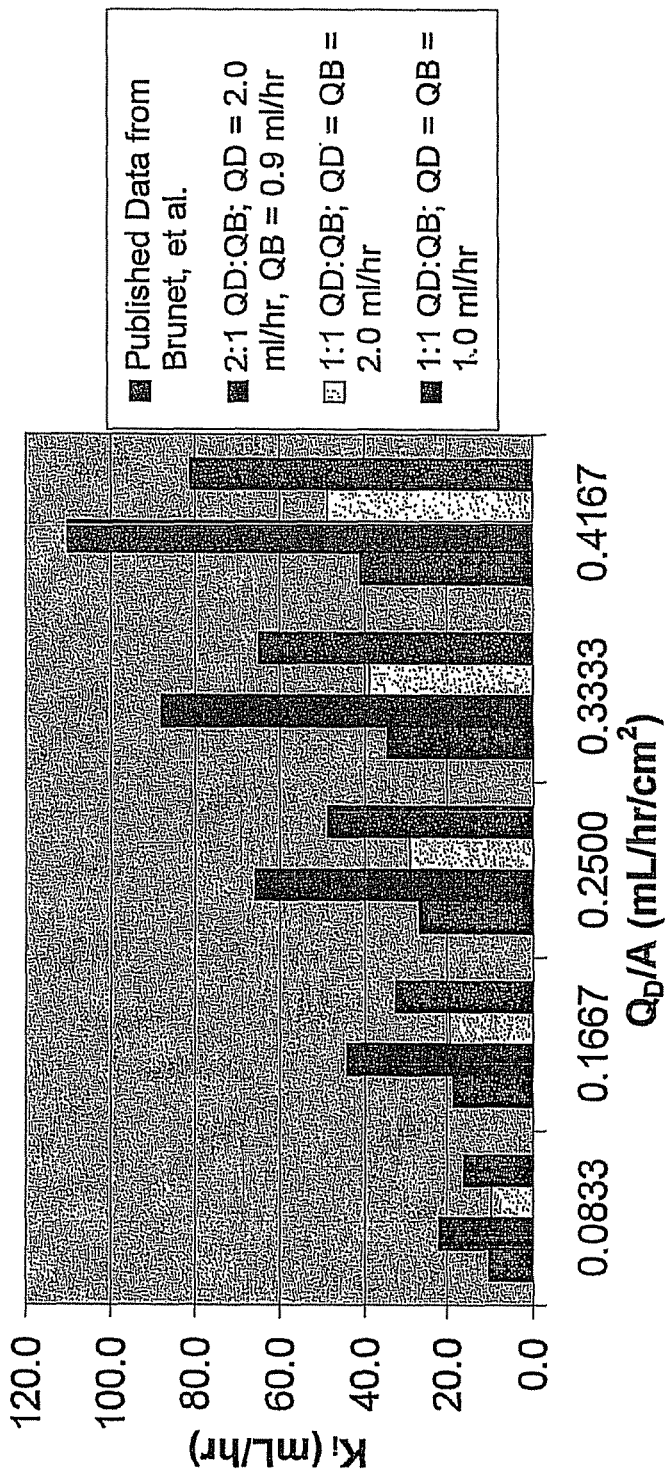
FIG. 6 is a chart depicting normalized experimental urea clearance obtained by exemplary ultrafiltration experiments using the system of FIG. 4, and a comparison of the experimental urea clearance with published data from the reference: S. Brunet, M. Leblanc, D. Geadah, D. Parent, S. Courteau and J. Cardinal, "Diffusive and convective solute clearances during continuous renal replacement therapy at various dialysate and ultrafiltration flow rates," *Am. J Kidney Dis.* 34 486-492 (1999)

As the fluids moved through their respective layers, samples from each flow stream were taken at various time points, up to five hours, and analyzed for final concentration levels. The temporal distribution of urea and creatinine concentration in the vascular and dialysate flows (see FIG. 5) were used to determine solute clearances and solute reduction rates. Finally, the calculated clearance values for urea and creatinine obtained here were normalized with respect to current hemodialysis parameters, including overall surface area and flow rate, and compared with published clearance values for overall efficiency (see FIG. 6).

The results of the ultrafiltration experiments illustrated promising results with regard to the clearance of uremic solutes (i.e., urea and creatinine) from a vascular stream into a dialysate stream in these micro-fabricated devices, especially when compared to conventional hemodialysis clearances. When the data is normalized and compared to conventional hemodialysis parameters, including total surface area for filtration, total internal volume, and total flow rate through the system, these bilayer devices, such as that depicted in FIG. 4, show a two-to-three fold improvement over current published urea and creatinine clearance data that is representative of the efficiency of current hemodialysis therapies.

The concentration versus time data for urea and creatinine show slightly different trends with respect to the dialysate-side clearances. However, both sets of data, suggest that an approximate 2:1 vascular:parenchymal flow rate ratio, where QB=0.9 ml/hr and QD=2.0 ml/hr, is the optimal ratio for the clearance of both solutes, which is the ratio used in conventional hemodialysis. This can be attributed to the establishment of a higher concentration gradient of solute between the vascular and parenchymal networks when the vascular fluid is allowed to remain in device 110 longer, relative to the parenchymal fluid.

The normalized data for both urea and creatinine clearance show that these bilayer devices are significantly to moderately more efficient at clearing uremic solutes from an incoming vascular stream than conventional hemodialysis membranes, with urea clearance at a 2:1 flow rate ratio showing the most drastic improvement.

Figure 7:
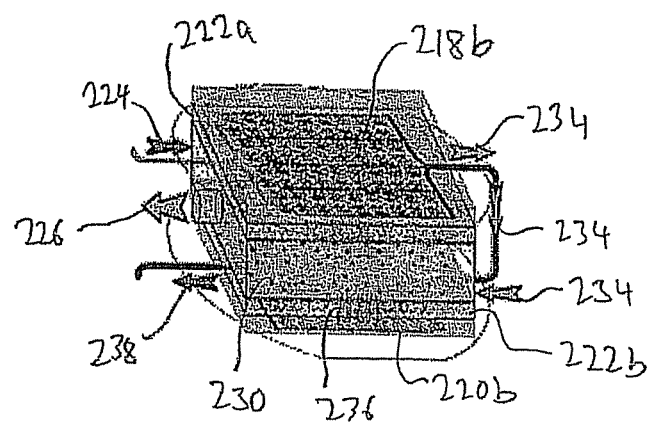
FIG. 7 is a schematic diagram illustrating a renal ultrafiltration and reabsorption device constructed in accordance with the present invention illustrating, among other things, the flow of blood therein.
Figure 8:
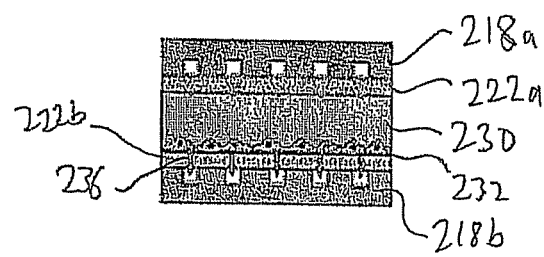
FIG. 8 is a cross sectional schematic diagram of the device shown in FIG. 7.
Figure 9:
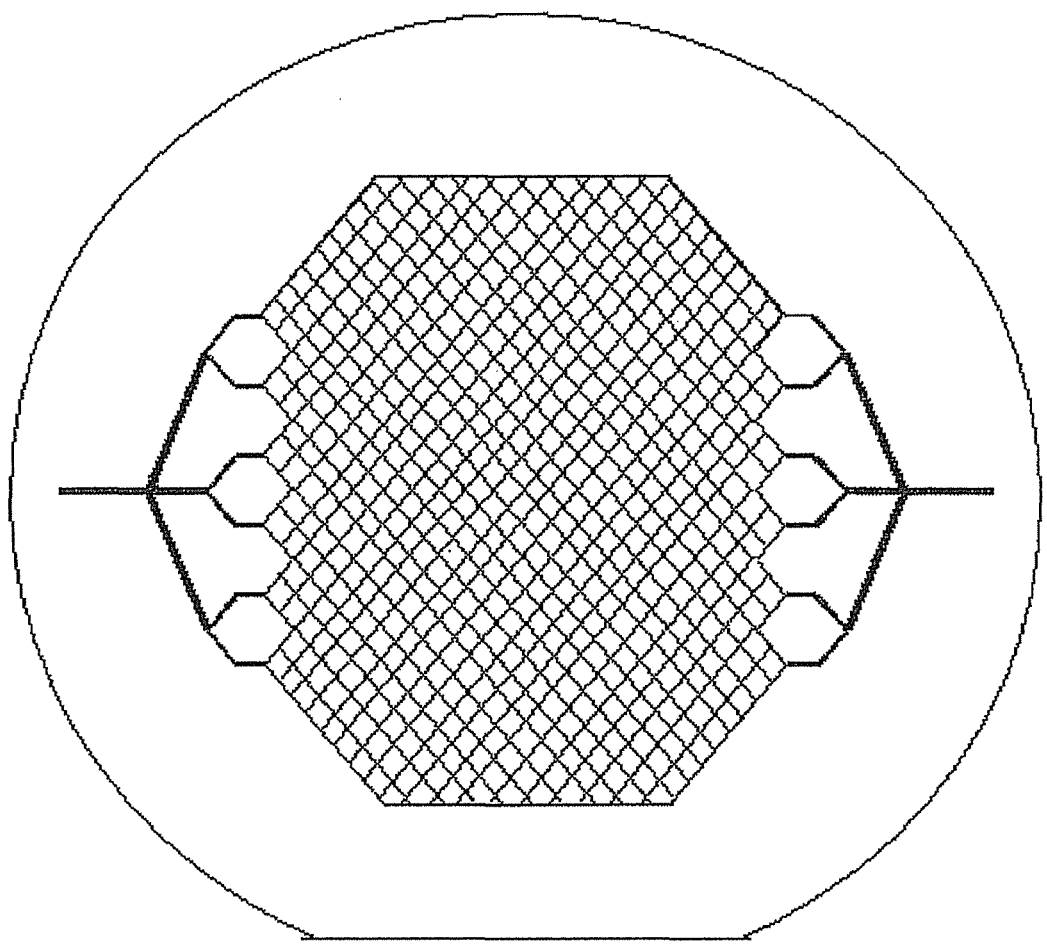
FIG. 9 shows a sample vascular branching network pattern used for silicon and pyrex wafer micromachining.

As shown in FIGS. 7-8, an exemplary extracorporeal renal unit 210 includes a mold layer 218a having a vascular network 220a disposed thereon for ultrafilitration, a first porous biocompatible membrane 222a adjacent thereto, a mold layer 218b having a vascular network 220b disposed thereon, a second porous biocompatible membrane 222b adjacent thereto, and a tubule chamber 230 positioned between membranes 222a and 222b having renal proximal tubule cells 232 disposed therein for the reabsorption of electrolytes. Alternatively, human or animal cells other than renal cells may be cultured or secured in device instead of or in addition to tubule cells in chamber 230 or another location within device 210.

Blood flow 224 enters device 210 and contacts mold layer 218a. Ultrafiltrate blood flow 234, and ultrafiltration 228 through membrane 222a, are directed to chamber 230 where exposure to proximal tubule cells occurs. Reabsorption flow 236 from chamber 230 is drawn through membrane 222b to mold layer 218b, while treated blood (i.e., ultrafiltrate and reabsorption) flow 238 and filtered blood/dialysate flow 226 exit device 210.

Having thus described in detail preferred embodiments of the present invention, it is to be understood that the invention defined by the appended claims is not to be limited to particular details set forth in the above description, as many apparent variations thereof are possible without departing from the spirit or scope of the present invention.

For example, devices with greater amounts of layers, such as between about 50 and 2000 layers, more preferably between about 100 and 1000 layers and most preferably about 500 layers stacked together, can be constructed in accordance with the present invention and using the process techniques described above.

Also, alternate methods for fabricating a device in accordance with the present invention include the use of the assembly processes described herein with rolling or folding schemes, rather than stacking methods, to provide high-throughput systems capable of reproducing organ function. Other alternatives include the use of laser machining, roll machining, injection molding and other techniques for machining of polymers or other suitable materials to generate layers for these filtration devices.

Another set of alternative methods for generating blood filtering devices in accordance with the present invention involve the use of monolithic structures rather than stacked sandwich structures with membranes and fluidic layers, as is described in International PCT Application US04/16059, filed on May 21, 2004, and incorporated herein by reference. In such devices individual layers of the comprise channels having multiple cell types (e.g., organ-specific cells and a vascular supply) divided by membrane. Each layer comprises channels divided longitudinally into two compartments by a centrally positioned membrane, with each compartment containing a different cell type.

In another embodiment, the device of the invention are augmented by the addition of active microdevices, such as pumps, valves and sensors, to monitor the performance and to actively contribute to the filtration process by altering the flows, pressures, distribution of blood components, and other critical parameters to enhance filtration. For example, micropumps, microvalves and microsensors have been developed using MEMS processes for a wide range of medical and non-medical applications, including drug delivery, bioanalysis, drug discovery and clinical diagnostics. Pumps, valves and sensors are well known in the art for use in in vivo applications in which both biocompatibility and hemocompatibility are factors, and therefore are suitable for integration with devices of the present invention. In one embodiment, devices of the invention can modulate the filtration process to preferentially filter certain classes of blood components over other components. For example, a renal assist device of the invention can preferentially filter urea and creatinine while maintaining a physiological concentration of electrolytes in the vascular network. This can be accomplished, for example, coupling the renal assist device with a pump which filters charged electrolytes differently than urea and creatinine.

Further modifications and variations of the methods and devices described herein, other than, and including those described above, will be obvious to those skilled in the art, and are intended to be encompassed by the following claims.

We claim:

1. An apparatus which duplicates the functionality of a physiological system, comprising:
    a) a first mold defining upper and lower surfaces, wherein the lower surface of the first mold includes acellular microchannels formed thereon to create a microvascular network for circulation of fluids, wherein the acellular microchannels begin at one or more inlets, serially branch into a large array of acellular microchannels, and then converge back into one or more acellular microchannels at one or more outlets;
    b) a second mold defining upper and lower surfaces, wherein the upper surface of the second mold includes acellular fluidic microchannels formed thereon; and
    c) a semi-permeable membrane defining an upper surface and a lower surface, wherein the upper surface of the membrane is secured adjacent to the lower surface of the first mold and the lower surface of the membrane is secured adjacent to the upper surface of the second mold, wherein small molecules are filtered from fluid in the microvascular network of the first mold through the semi-permeable membrane to the acellular fluidic chambers of the second mold.

2. The apparatus of claim 1, further comprising nutrient supply and excretion removal conduits in fluid communication with the apparatus.

3. The apparatus of claim 2, further comprising pumping means for circulating fluid through the apparatus.

4. The apparatus of claim 1, further comprising additional molds stacked upon the first and second molds to form about 8 to about 2000 layers.

5. The apparatus of claim 1, wherein the semi-permeable membrane is made of a material selected from the group consisting of cellulose, PolyDiMethylSiloxane, PolyMethylMethacrylate, PolyEtherSulfone, PolySulfone, PolyCarbonate, PolyLactide-co-Glycolide, PolyCaproLactone and Biorubber.

6. The apparatus of claim 1, wherein there is a pattern of microchannels in each of the first and second molds and the pattern in the first mold is identical to the pattern in the second mold.

7. The apparatus of claim 1, wherein there is a pattern of microchannels in each of the first and second molds and the pattern in the first mold is non-identical to the pattern in the second mold.

8. The apparatus of claim 1, further comprising a coating on at least one surface that includes a blood clot-preventing compound.

9. The apparatus of claim 1, wherein the semi-permeable membrane is biodegradable.

10. The apparatus of claim 1, wherein the semi-permeable membrane has pores of between about 0.01 and about 20 μm.

11. The apparatus of claim 1, wherein at least one of the molds comprises through-holes.

12. The apparatus of claim 1, wherein the fluid is blood.

13. The apparatus of claim 1, wherein the acellular microchannels are about 100 μm to about 900 μm in width and height.

* * * * *